US012788232B2

(12) United States Patent
Freitag et al.

(10) Patent No.: US 12,788,232 B2
(45) Date of Patent: Nov. 10, 2026

(54) ENDOSCOPY EQUIPMENT WITH RETRACTABLE VIDEO UNIT

(71) Applicant: NOVATECH SA, La Ciotat Cedex (FR)

(72) Inventors: Lutz Freitag, Hemer (DE); Manuel Gerold, Kloten (CH)

(73) Assignee: Novatech SA, La Ciotat Cedex (FR)

( * ) Notice: Subject to any disclaimer, the term of this patent is extended or adjusted under 35 U.S.C. 154(b) by 977 days.

(21) Appl. No.: 17/915,801

(22) PCT Filed: Mar. 29, 2021

(86) PCT No.: PCT/EP2021/058118

§ 371 (c)(1),
(2) Date: Apr. 17, 2023

(87) PCT Pub. No.: WO2021/198159

PCT Pub. Date: Oct. 7, 2021

(65) Prior Publication Data

US 2023/0248228 A1 Aug. 10, 2023

(30) Foreign Application Priority Data

Mar. 30, 2020 (DE) ..................... 10 2020 108 748.9

(51) Int. Cl.
*A61B 1/012* (2006.01)
*A61B 1/018* (2006.01)
(Continued)

(52) U.S. Cl.
CPC ............ *A61B 1/0125* (2013.01); *A61B 1/018* (2013.01); *A61B 1/04* (2013.01); *A61B 1/05* (2013.01)

(58) Field of Classification Search
CPC ......... A61B 1/0125; A61B 1/018; A61B 1/04; A61B 1/05; A61F 2/95; A61F 2/9522;
(Continued)

(56) References Cited

U.S. PATENT DOCUMENTS 5,803,080 A * 9/1998 Freitag .................... A61F 2/958
128/207.14
6,402,760 B1 * 6/2002 Fedida ...................... A61F 2/95
604/528
(Continued)

FOREIGN PATENT DOCUMENTS

| | | | |
|---|---|---|---|
| BY | 11399 U * | 6/2017 |
| DE | 102009056448 | 6/2011 |
| WO | WO 2018/197870 | 11/2018 |

OTHER PUBLICATIONS

International Search Report issued by the European Patent Office on Jun. 24, 2021 in International Application PCT/EP2021/058118.

*Primary Examiner* — Anhtuan T Nguyen
*Assistant Examiner* — Shankar Raj Ghimire
(74) *Attorney, Agent, or Firm* — Henry M. Feiereisen LLC

(57) ABSTRACT

An endoscopy device for introducing an expandable body into a cavity includes a first endoscope having a working channel, a further endoscope accommodating the expandable body and insertable with the expandable body in the working channel of the first endoscope, and a video unit located in the further endoscope in parallel relation to the expandable body and having a distal end situated next to a distal end of the expandable body in order to place the expandable body under visual control in the cavity prior to expansion. The video unit is designed to form an abutment at a proximal end of the expandable body after positioning of the expandable body and when the further endoscope is withdrawn.

6 Claims, 7 Drawing Sheets

(51) Int. Cl.
*A61B 1/04* (2006.01)
*A61B 1/05* (2006.01)

(58) Field of Classification Search
CPC ............ A61F 2/9526; A61F 2002/9528; A61F 2002/9534; A61F 2/962
See application file for complete search history.

(56) References Cited

U.S. PATENT DOCUMENTS

| | | | | |
|---|---|---|---|---|
| 7,727,169 | B1 * | 6/2010 | Lewkowicz | A61B 5/073 600/593 |
| 8,311,312 | B1 * | 11/2012 | Richardson | G01N 21/952 382/141 |
| 8,517,921 | B2 | 8/2013 | Tremaglio et al. | |
| 8,801,606 | B2 * | 8/2014 | Sheetz | A61B 1/041 600/101 |
| 9,402,531 | B2 * | 8/2016 | Chin | A61B 1/00154 |
| 2002/0004663 | A1 * | 1/2002 | Gittings | A61F 2/064 606/153 |
| 2005/0070794 | A1 * | 3/2005 | Deal | A61M 25/0662 600/434 |
| 2007/0123971 | A1 * | 5/2007 | Kennedy, II | A61F 2/95 623/1.11 |
| 2008/0183272 | A1 * | 7/2008 | Wood | A61B 90/30 606/228 |
| 2008/0312747 | A1 * | 12/2008 | Cameron | A61F 2/915 623/23.7 |
| 2009/0069822 | A1 * | 3/2009 | Takahashi | A61B 17/068 606/139 |
| 2012/0041533 | A1 * | 2/2012 | Bertolino | A61F 2/966 623/1.11 |
| 2012/0041534 | A1 * | 2/2012 | Clerc | A61F 2/966 600/109 |
| 2014/0088358 | A1 | 3/2014 | Banik et al. | |
| 2016/0173829 | A1 * | 6/2016 | Olsson | H04N 7/183 348/84 |
| 2016/0374546 | A1 * | 12/2016 | Berbee | A61B 1/05 600/109 |
| 2017/0135830 | A1 | 5/2017 | Harkin et al. | |
| 2018/0250484 | A1 * | 9/2018 | McCormick | A61B 1/05 |
| 2021/0251789 | A1 * | 8/2021 | Ouyang | A61B 1/00052 |
| 2023/0363729 | A1 * | 11/2023 | Murakami | A61B 6/461 |

* cited by examiner

ENDOSCOPY EQUIPMENT WITH RETRACTABLE VIDEO UNIT

CROSS-REFERENCES TO RELATED APPLICATIONS

This application is the U.S. National Stage of International Application No. PCT/EP2021/058118, filed Mar. 29, 2021, which designated the United States and has been published as International Publication No. WO 2021/198159 A1 and which claims the priority of German Patent Application, Serial No. 10 2020 108 748.9, filed Mar. 30, 2020, pursuant to 35 U.S.C. 119(a)-(d).

BACKGROUND OF THE INVENTION

The invention relates to an endoscopy device and to a method for the introduction of an expandable body into a cavity by means of such an endoscopy device.

An endoscope is used for minimally invasive surgical procedures on humans and animals as well as in technology for the visual inspection of cavities that are difficult to access. Endoscopes were originally developed for human medical diagnostics. Endoscopes are also used for the placement of stents. For this purpose, an external endoscope is typically inserted up to the constriction where the stent is to be placed. An inner endoscope is then pushed into the outer endoscope. This inner endoscope is loaded with the stent. When the stent is in the correct position, the inner endoscope is withdrawn, so that the stent is released. A rigid pusher holds the stent in position when the inner endoscope is withdrawn.

However, it is technically difficult to position the stent while simultaneously withdrawing the inner endoscope and still also guiding the outer endoscope. In human medicine, the placement of stents or expandable bodies in general takes place under X-ray control and requires great skill on the part of the operator.

Video sticks are known which now also have relatively small diameters. In bronchoscopy, it is possible to initially move the endoscope to the correct position using video control before the stent is pushed out of the endoscope. However, the video stick has to be withdrawn first and a pusher has to be inserted into the endoscope in order to release the stent. A video optic is normally a rigid optic that is not suitable for exerting compressive forces.

The invention is based on the object to provide an endoscopy device for the introduction of an expandable body into a cavity, which device simplifies the placement of an expandable body in the cavity. Furthermore, a suitable method for the placement of an expandable body under video control is to be provided, which method can be carried out in a simplified manner.

SUMMARY OF THE INVENTION

In terms of an endoscopy device, this object is attained as set forth hereinafter.

In terms of the method for the introduction of an expandable body, the object is attained as set forth hereinafter.

The respective dependent patent claims relate to advantageous refinements of the invention.

The endoscopy device according to the invention is not limited to applications in human medicine or veterinary medicine. The endoscopy device can be provided for any cavity in the human or animal body or can also be provided for use in technical areas.

The endoscopy device according to the invention is particularly suitable for placing stents in the trachea or esophagus.

The endoscopy device includes a first endoscope with a working channel into which a further endoscope with the expandable body to be introduced can be inserted. A video unit is located in the further endoscope parallel to the expandable body. A distal end of the video unit is situated next to a distal end of the expandable body in order to place the expandable body into the cavity under visual control.

The video unit is not used separately or divorced from the expandable body, but parallel to the expandable body, i.e. it is arranged locally parallel and at the same time in the further, inner endoscope. This makes it possible to use the video unit to place the distal end of the expandable body under video control at the desired location, in particular behind a constriction in the area of the cavity. The endoscope, in which the expandable body is located, is now held in position and the video unit is used as an abutment.

The video unit can have two different diameter regions. A distal region of the video unit preferably has a small diameter, in particular no more than 4 mm. Parallel to this region is the expandable body inside the endoscope.

The length of the region that is smaller in diameter is adjustable. This length can be shortened via one or more spacer elements. The spacer elements can be fastened to the video unit to conform to bodies that can be expanded to different lengths. The fastening can be established on the thinner, distal region of the video unit or also in the transition to a proximally adjoining region that is greater in the transition. The connection between the video unit and the at least one spacer element is detachable and held captive, so that the at least one spacer element cannot remain in the endoscope even when it is pulled back. The connection can be made in a form-fitting manner or also by a clamping plug connection. Provision may made for additional securing means for fastening the at least one spacer element.

The endoscope used may involve in particular an endoscope tube made of a low-friction plastic, e.g. PTFE, or an endoscope tube with a suitable inner and/or outer coating, with the coating reducing friction and made in particular of PTFE. A folded stent can be introduced into the endoscope tube as an expandable body, e.g. a stent made of a polymer material, or an expandable body is located in the endoscope tube before it is positioned in the cavity. In a first embodiment, a further region of greater diameter can adjoin proximally the distal end of the video unit with the stated smaller diameter. This region of greater diameter serves as a direct or indirect abutment for the expandable body when the endoscope tube is withdrawn. In this context, directly means that the expandable body comes into direct contact with the region of greater diameter. Indirect means that the region of greater diameter serves as an abutment, but at least one spacer element is arranged between the expandable body and the region of greater diameter, on which the expandable body is supported. In both cases, the region of greater diameter of the video unit serves as pusher.

When the expandable body has been pushed out and deployed, the video unit can also be withdrawn. During withdrawal of the video unit, the position of the expandable body can be checked immediately.

The difference in diameter between the regions of the video unit is sized sufficiently to provide an abutment for the expandable body. In particular, the diameter ratios between the adjoining regions have values of 2 to 3, so that the diameter in the greater region is twice to three times as great, for example 8 to 12 mm, with a diameter of the smaller region of 4 mm. For applications in bronchoscopy, diameters of e.g. 3 to 4 mm are advantageous. For other applications, e.g. in the area of the esophagus, diameters of 6 mm are also possible.

Alternatively, a video unit without such a gradation can be withdrawn after positioning the expandable body until it abuts the proximal end of the expandable body. Since the video unit offers the possibility of visual control, the exact position of the distal end of the video unit is easy to adjust. The distal end of the video unit itself can now serve as an abutment. With this approach, it is possible to use a uniformly slim video unit that does not have different diameter regions. However, it is a prerequisite that the expandable body has a sufficiently large end face upon which the endoscope is able to come to rest as an abutment without the expandable body slipping off. In an advantageous refinement of the invention, the video unit is flexible, with the flexibility preferably being greater in the region of its distal end than at the proximal end. Limited flexibility is of advantage in certain applications, in particular bronchoscopy.

The method according to the invention provides to initially position an outer endoscope in the cavity and then to insert an inner endoscope with the video unit, with a distal end of the video unit being placed beforehand next to the distal end of the expandable body in the inner endoscope. The term "next" means that the distal ends of the video unit and the expandable body are flush, or at least substantially flush. Matching bodies that can be expanded to different lengths can be realized via spacer elements. The inner endoscope is placed in the cavity up to the desired depth under video control using the video unit. The video control does not exclude the possibility of an additional X-ray control. After the inner endoscope has been placed correctly or after placement of the expandable body, the latter is expanded in the next step. For this purpose, the expandable body is held in the desired position and the endoscope enveloping it is withdrawn. This requires an abutment to overcome the friction between the expandable body and the wall of the working channel which the expandable body bears against. The video unit itself serves as the abutment by withdrawing the video unit and placing it at the proximal end of the expandable body. The endoscope, which prefers the expandable body and only holds it through static friction, can now be withdrawn.

DETAILED DESCRIPTION OF PREFERRED EMBODIMENTS

Alternatively, the video unit remains in the original position because it has an enlarged diameter region upon which the proximal end of the expandable body is already supported directly or indirectly via spacer elements. In this case, only the endoscope but not the video unit has to be withdrawn. The expandable body is released and is now expanding in the cavity. "Expanding" also relates to the mere unfolding/unrolling, e.g. of a silicone stent, i.e. the transition inside the endoscope tube from the transport position of smaller diameter to a release position outside the endoscope tube. When self-expanding metal stents are involved, expansion/release means an increase in diameter to conform to the cavity. The video unit can then be withdrawn under video control.

A refinement further provides that another endoscope is placed as an abutment at the proximal end of the expandable body. This involves in particular an endoscope/instrument that has a gripping device at its distal end. This allows the position of the expandable body to be corrected in relation to its longitudinal axis, for example when the expandable body has a flattened side which is intended to come into contact with a corresponding region of the cavity. A gripping device within the meaning of the invention can have a fixed or actuatable gripper. In the simpler case, the gripping device is a coupling, such as e.g. a tongue and groove arrangement. The gripping device has a groove which can be clamped onto the front, proximal edge of the expandable body or inserted with play, e.g. in order to rotate the expandable body. An actuatable gripper can be constructed like tongs with a movable tong head. The video unit may moreover include a lateral longitudinal groove that serves as a channel for conduction of gas from the proximal to the distal end. The channel serves to supply oxygen to the patient in applications in the field of bronchoscopy.

BRIEF DESCRIPTION OF THE DRAWING

The invention is explained hereinafter with reference to purely schematic drawings and illustrated exemplary embodiments. It is shown in:

FIG. 1 shows an endoscopy device 1 for introducing an expandable body 2 (stent) into a cavity 3. The cavity 3 has a constriction 4. The expandable body 2 is to be placed in the area of this constriction 4 using the endoscopy device 1. For this purpose, a first endoscope 5 with a working channel 6 is inserted into the cavity 3 up to the desired depth. The expandable body 2 is situated in a further endoscope 7 which is inserted into the first endoscope 5. In this further endoscope 7, of which only the endoscope tube is shown, there is a video unit 8 with a significantly smaller diameter. The video unit 8 has a diameter of 4 mm, for example. The further endoscope 7 has a diameter of 12 to 14 mm. The video unit 8 has a distal end 9 which is located at, i.e. immediately adjacent to, the distal end 10 of the expandable body 2. The expandable body 2 is thus parallel to the video unit 8. The position of the distal end 9 of the video unit 8 is equivalent to the position of the camera of the endoscopy device 1, so that the expandable body 2 can be introduced under video control precisely up to behind the distal end of the constriction 4.

FIG. 2 shows an end view of the position of the folded, expandable body 2 in the further endoscope 7 parallel to the video unit 8 with its distal end 9, which at the same time embodies the video camera. The further endoscope 7 is made in particular of PTFE or has an inner coating made of PTFE.

FIG. 3 shows the next step of inserting the expandable body 2. For this purpose, the further endoscope 7 is moved forward until the distal end 9 of the video unit 8 has passed the constriction 4 in the cavity 3. The further endoscope 7 is now withdrawn in order to release the expandable body 2 in this position. This requires an abutment at the distal end 11 of the expandable body 2.

The abutment is created by withdrawing the video unit 8 by the length of the expandable body 2. This is shown in FIG. 4. The distal end 9 of the video unit 8 is now situated at the proximal end 11 of the expandable body 2. The video unit 8 is held in this position and the further endoscope 7 is withdrawn. FIGS. 5 and 6 show this process in two chronologically consecutive steps. In FIG. 5, the expandable body 2 is only partially released. In FIG. 6, the expandable body 2 is fully released. The constriction 4 is supported from the inside. The clear passage cross section of the cavity 3 has been enlarged and the correct position of the expandable body 2 can be checked via the video unit 8.

Figure 5:
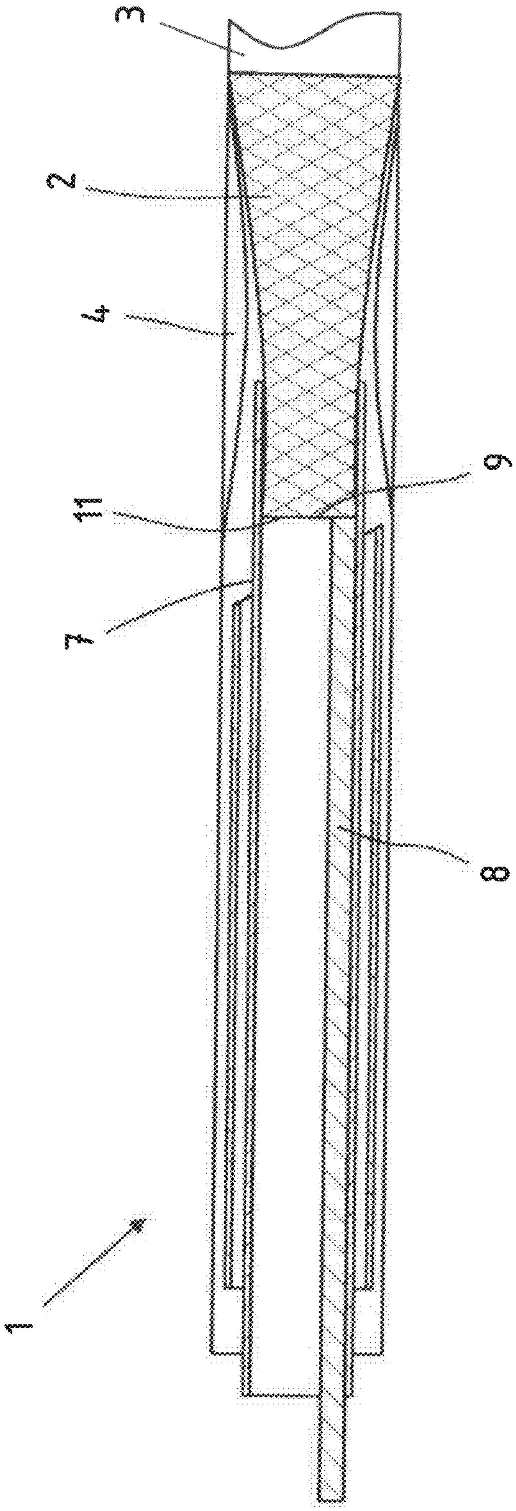
FIG. 5 a longitudinal section through the endoscopy device of FIG. 4, with the further endoscope being partially withdrawn.
Figure 6:
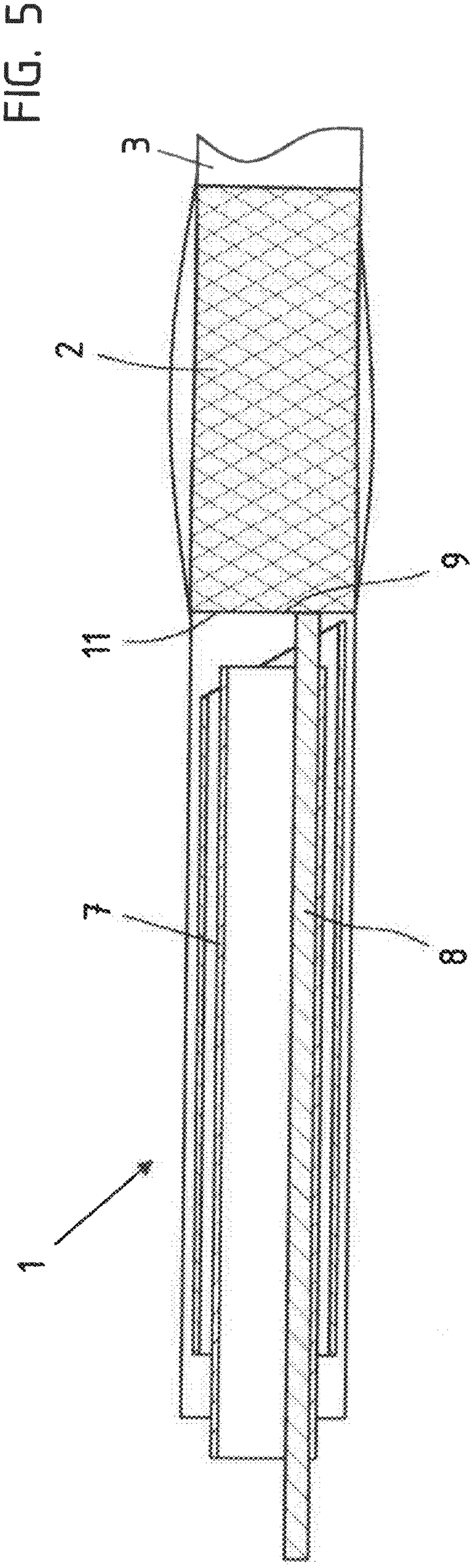
FIG. 6 a longitudinal section through the endoscopy device of FIG. 5, with the further endoscope having been withdrawn completely into the first endoscope and the expandable body having been released.
Figure 7:
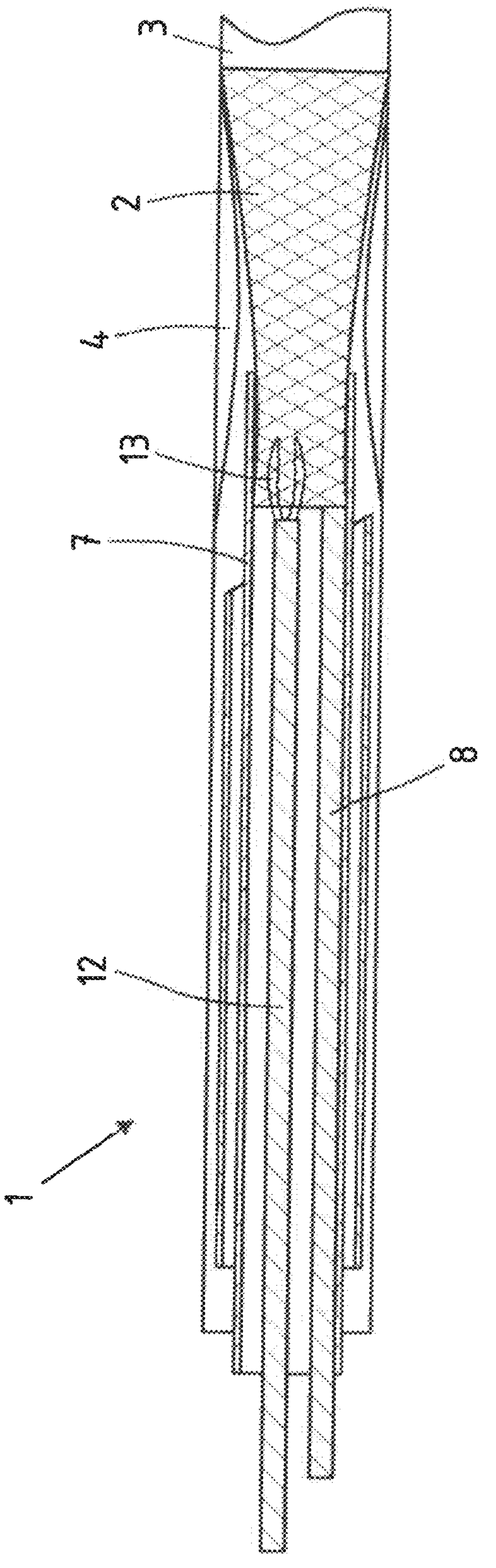
FIG. 7 a longitudinal section through an endoscopy device according to the illustration in FIG. 5, with a further endoscope with a gripping device having been introduced parallel to the video unit.
Figure 8:
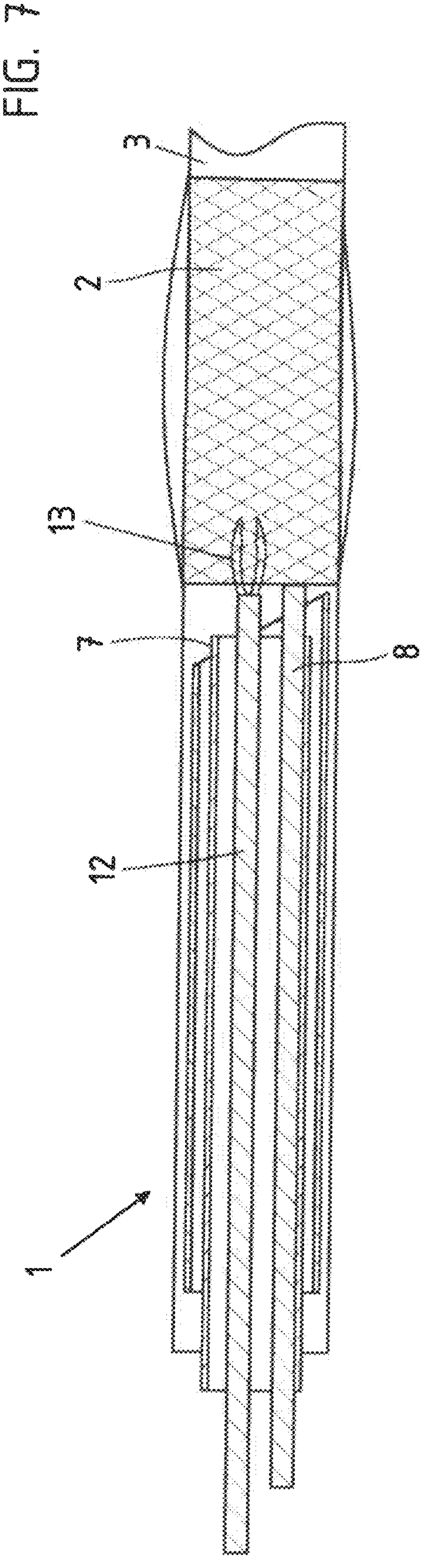
FIG. 8 a longitudinal section through the endoscopy device according to FIG. 6, with another endoscope additionally manipulating the distal end of the expandable body with a gripping device.

Since not all expandable bodies 2 are necessarily rotationally symmetrical, there may be the necessity to rotate the expandable body 2, for example with a flattened side, into a special position. For this purpose, it is possible to use a further endoscope 12 with a gripping device 13, as shown in FIGS. 7 and 8 analogously to the chronological sequence of FIGS. 5 and 6. The expandable body 2 can be rotated about a longitudinal axis by the gripping device 13. It is also possible to create an abutment for the expandable body 2 via the further endoscope 12 and the gripping device 13. In this case, the video unit 8 is only used for support or can also be pulled back for visual control, when the support is established exclusively via the other endoscope 12 with the gripping device 13. The result is a correctly positioned expandable body 2 in the cavity 3.

Figure 1:
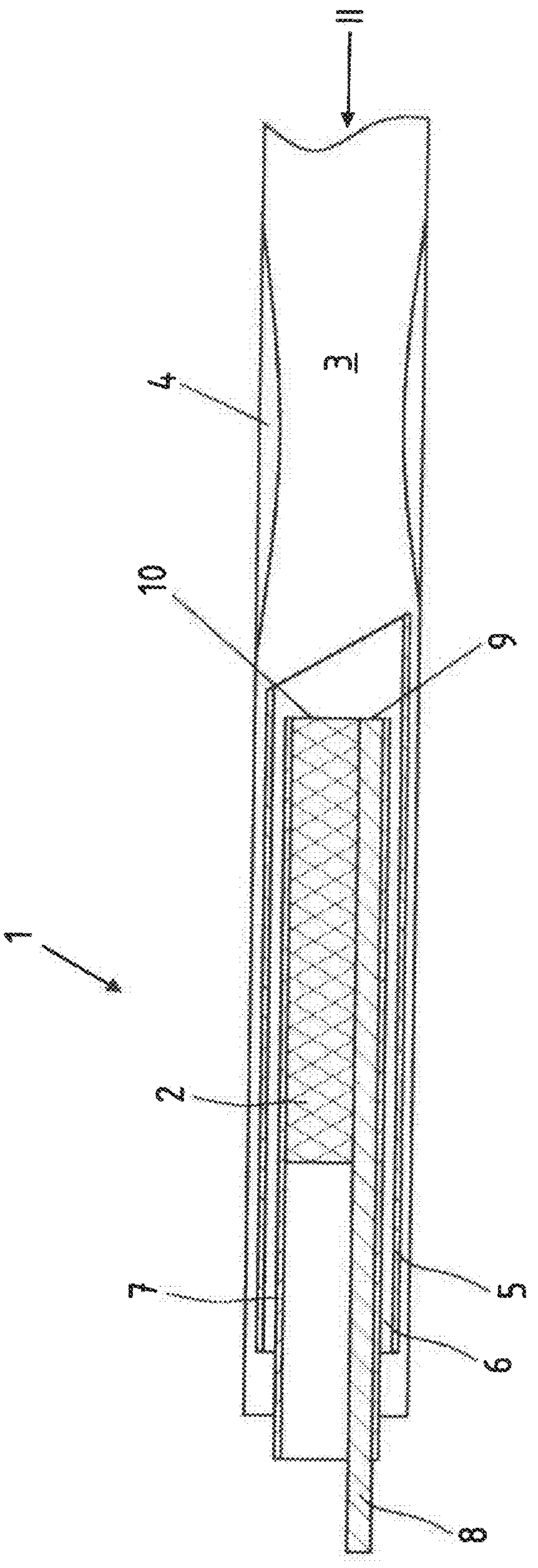
FIG. 1 a side view of a first embodiment of the endoscopy device.
Figure 2:
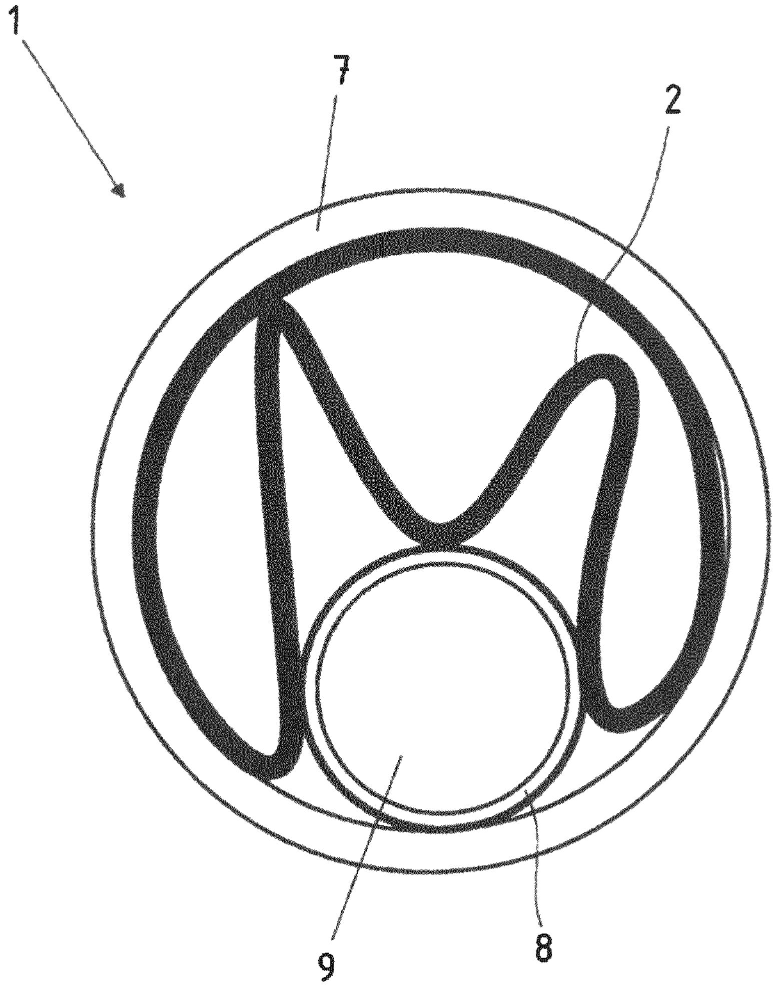
FIG. 2 an end view in direction of arrow II of the expandable body in folded form.
Figure 3:
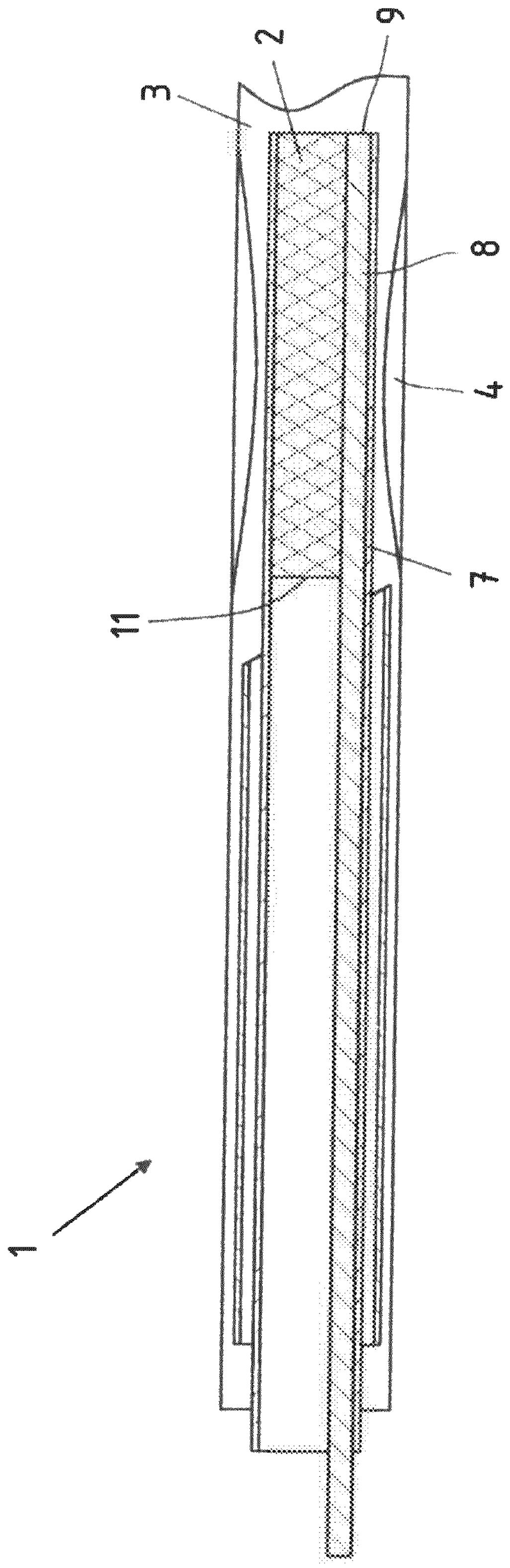
FIG. 3 a longitudinal section through the endoscopy device, with the expandable body being advanced into the desired position.
Figure 4:
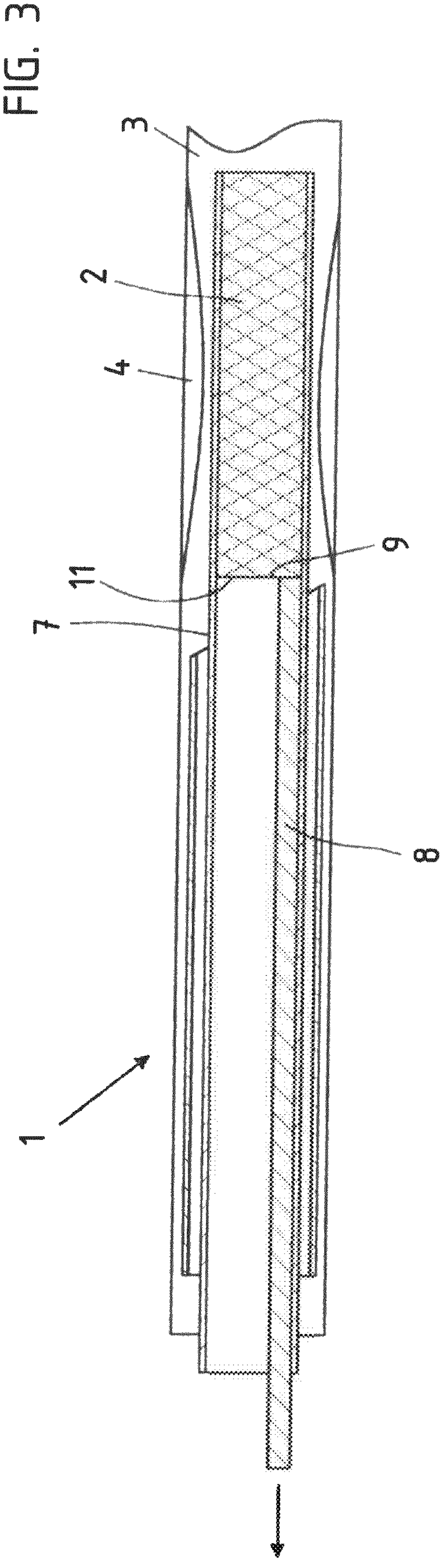
FIG. 4 a longitudinal section through the endoscopy device of FIG. 3, with the video unit being withdrawn.
Figure 9:
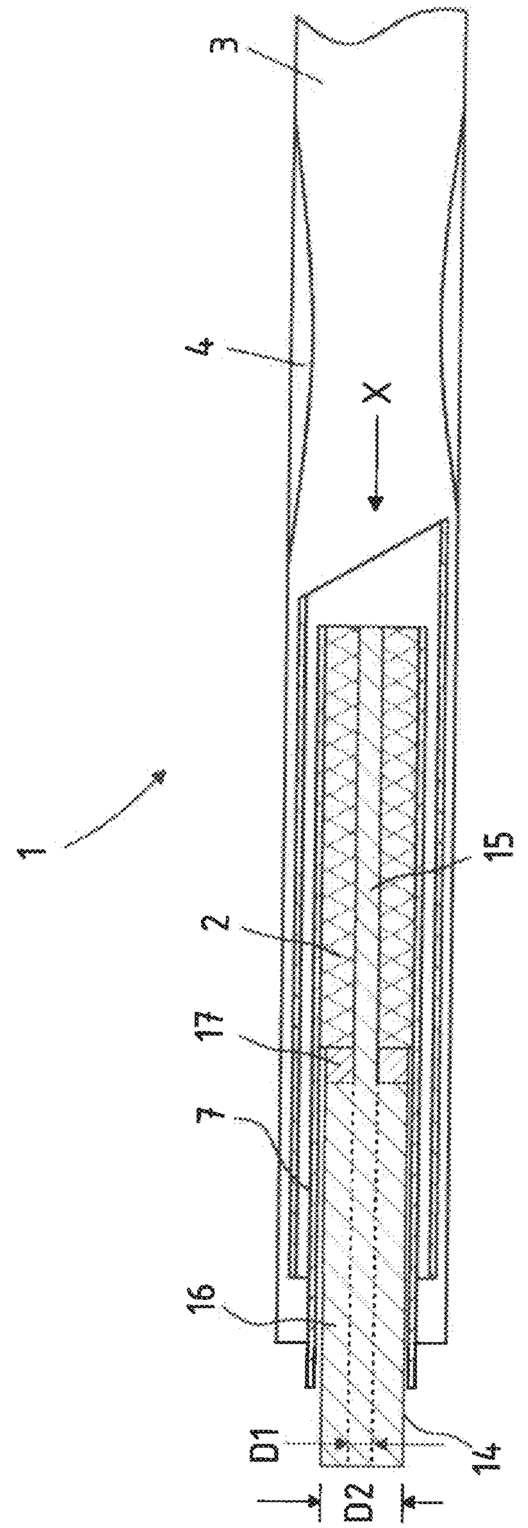
FIG. 9 a longitudinal section through a further embodiment of an endoscopy device with a video unit with a graduated diameter region.
Figure 10:
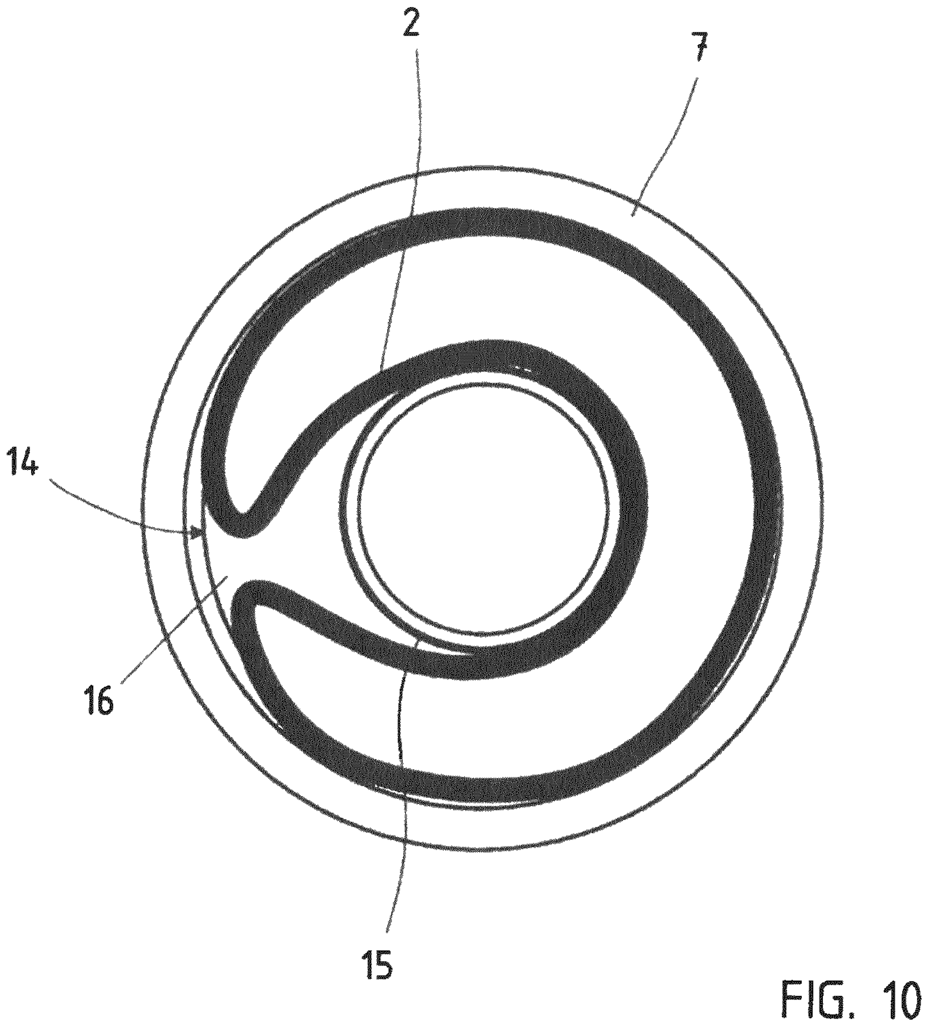
FIG. 10 a view of the endoscopy device according to the arrow X in FIG. 9.

The exemplary embodiment of FIG. 9 shows an alternative embodiment with a different type of video unit 14, This video unit 14 also serves as an abutment for the expandable body 2. The video unit 14 has a distal region 15 with a smaller diameter. As in the exemplary embodiment in FIG. 1, this distal region 15 is situated parallel to the expandable body 2. In this case, however, the distal region 15 of smaller diameter is located concentrically within the further endoscope 7 and not at the border, as is illustrated in FIG. 1. The end view of FIG. 10 shows that as a result the expandable body 2 bears slightly differently around the video unit 14 and assumes a substantially U-shaped form.

The video unit 14 has adjacent to the distal region 15 a region 16 of greater diameter. The ratio of the different diameters D1, D2 is 1 to 2 to 1 to 3.

The procedure for positioning the expandable body 2 is simpler than in the exemplary embodiment of FIG. 1. The endoscope 7 with the expandable body 2 and with the video unit 14 have been brought, like in the exemplary embodiment of FIG. 1, to the desired position in the area of the constriction 4. The further endoscope 7 is then withdrawn, while the video unit 14 remains in position. The video unit 14 does not have to be withdrawn as a result of the integrated support for the expandable body 2, but can remain in the original position. After the body 2 has been expanded, the video unit 14 can be withdrawn through the expanded body 2 in order to carry out a video check of the positioning. A spacer element 17 is releasably disposed and held captive next to and adjacent to the transition between the greater diameter region 16 and the smaller diameter region 15. By using spacer elements 17 of different lengths, the position of the expandable body 2 within the endoscope 7 can be adjusted so that its distal end coincides with the distal end of the video unit 14 as much as possible.

The invention claimed is:

1. An endoscopy device for introducing an expandable body into a cavity, comprising:

a first outer endoscope having a first working channel;

a second inner endoscope accommodating the expandable body in a collapsed stat in a second working channel and insertable in the first working channel of the first endoscope; and a video unit disposed in the second working channel in parallel relation to the expandable body and having a distal end located next to a distal end of the expandable body, wherein the video unit is designed to be withdrawn, after placement of the second inner endoscope with the expandable body prior to expansion, with the distal end of the video unit forming after withdrawal of the video unit an abutment for a proximal end of the expandable body prior to expansion to prevent displacement of the expandable body in the cavity, when the second endoscope is withdrawn through the first working channel and the expandable body expands in the cavity.

2. The endoscopy device of claim 1, wherein the video unit is flexible.

3. The endoscopy device of claim 1, wherein the video unit has a flexibility which in an area of the distal end is greater than in an area of a proximal end thereof.

4. The endoscopy device of claim 1, further comprising a further endoscope disposed inside the second inner endoscope and having a gripping device disposed at a distal end of the further endoscope, said further endoscope configured to rotate the expandable body into a desired position.

5. A method for introducing an expandable body into a cavity, the method comprising:

positioning a first outer endoscope in the cavity;

inserting a video unit into a second inner endoscope, with video unit extending parallel to the expandable body and a distal end of the video unit disposed next to a distal end of the expandable body accommodated in the second inner endoscope;

pushing the second inner endoscope under video control by the video unit into the cavity to a desired depth;

creating an abutment at a proximal end of the expandable body by withdrawing the video unit until the distal end of the video unit is located at the proximal end of the expandable body; and withdrawing the second inner endoscope while the proximal end of the expandable body is supported on the distal end of the withdrawn video unit so as to release the expandable body.

6. The method of claim 5, further comprising:

placing as the abutment at the proximal end of the expandable body a further endoscope with a gripping device disposed at a distal end of the further endoscope; and rotating the expandable body with the gripping device into a desired position.

* * * * *